(12) United States Patent
Dolan

(10) Patent No.: US 7,087,043 B2
(45) Date of Patent: Aug. 8, 2006

(54) EXTERNAL URINARY CATHETER

(76) Inventor: Donald L. Dolan, 5 W. 900 South, Kouts, IN (US) 46347

( * ) Notice: Subject to any disclaimer, the term of this patent is extended or adjusted under 35 U.S.C. 154(b) by 393 days.

(21) Appl. No.: 10/375,065

(22) Filed: Feb. 28, 2003

(65) Prior Publication Data

US 2004/0034335 A1    Feb. 19, 2004

Related U.S. Application Data

(60) Provisional application No. 60/359,905, filed on Feb. 28, 2002.

(51) Int. Cl.
*A61F 5/44*    (2006.01)
(52) U.S. Cl. .................. 604/349; 604/351; 604/353
(58) Field of Classification Search ................ 604/349, 604/351, 353, 317, 327, 346–47, 347, 350
See application file for complete search history.

(56) References Cited

U.S. PATENT DOCUMENTS

| | | | |
|---|---|---|---|
| 3,339,551 A * | 9/1967 | Stoutenburgh | 604/349 |
| 3,405,714 A * | 10/1968 | Moss | 604/350 |
| 4,022,213 A * | 5/1977 | Stein | 604/350 |
| 4,117,845 A | 10/1978 | Brown | |
| 4,387,726 A * | 6/1983 | Denard | 600/573 |
| 4,432,357 A | 2/1984 | Pomeranz | |
| 4,588,397 A * | 5/1986 | Giacalone | 604/349 |
| 4,668,229 A | 5/1987 | Fago et al. | |
| 4,673,401 A * | 6/1987 | Jensen et al. | 604/353 |
| 4,759,753 A * | 7/1988 | Schneider et al. | 604/352 |
| 4,790,834 A | 12/1988 | Austin | |
| 5,263,946 A | 11/1993 | Klug | |
| 5,409,474 A | 4/1995 | Fleeman-Hardwick | |
| 5,478,334 A * | 12/1995 | Bernstein | 604/353 |
| 5,586,978 A | 12/1996 | Bayne | |
| 5,741,240 A | 4/1998 | Olsen | |
| 5,827,247 A | 10/1998 | Kay | |
| 5,827,249 A | 10/1998 | Jensen | |
| 6,068,618 A | 5/2000 | Anderson | |
| 6,221,447 B1 | 4/2001 | Munn et al. | |
| 6,280,425 B1 | 8/2001 | Del Guercio | |
| 6,296,627 B1 | 10/2001 | Edwards | |

* cited by examiner

*Primary Examiner*—Karin Reichle
(74) *Attorney, Agent, or Firm*—Shoemaker and Mattare

(57) ABSTRACT

An external urinary catheter includes a housing, an annular base, and a cap which are assembled to form a container which is placed over the penis to receive urine passing from the urethra. A fitting in the side of the container permits one to connect the container to a remote receptacle. A stretchable condom-like sleeve secured around the base prevents liquid leakage between the base and the penis.

3 Claims, 6 Drawing Sheets

EXTERNAL URINARY CATHETER

This application claims the benefit of U.S. provisional application 60/359,905, filed Feb. 28, 2002.

BACKGROUND OF THE INVENTION

This invention relates to the field of medicine, and more particularly to external urinary catheters for men.

Loss of continence may be embarrassing and is inconvenient. Prior inventors have proposed a variety of solutions to this problem. To collect urine from people who have diminished or no bladder control, a variety of absorbent pads and catheters have been developed. Pads are uncomfortable when wet, and may leak. Internal catheters also cause discomfort and may reduce the patient's mobility.

Some external urine collection devices have been designed for men. Typically, with such devices, the penis is placed in a urine receptacle leading to a remote disposal container. We refer to such devices as "external urinary catheters".

This invention provides an improved solution to the incontinence problem for men.

BRIEF DESCRIPTION OF THE DRAWINGS

In the accompanying drawings.

DESCRIPTION OF THE PREFERRED EMBODIMENT

Figure 1:
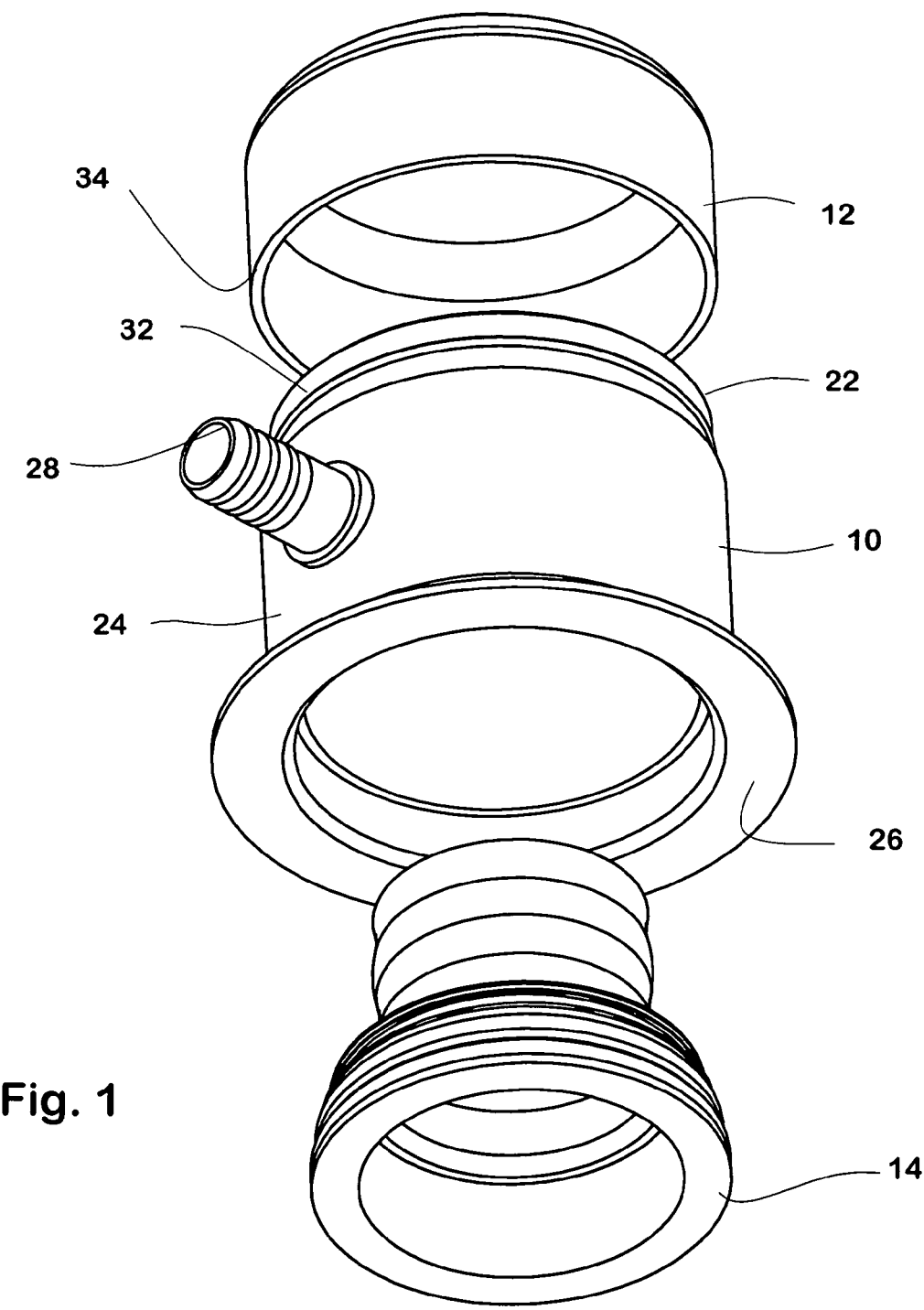
FIG. 1 is an exploded perspective view of an external male catheter embodying the invention.
Figure 2:
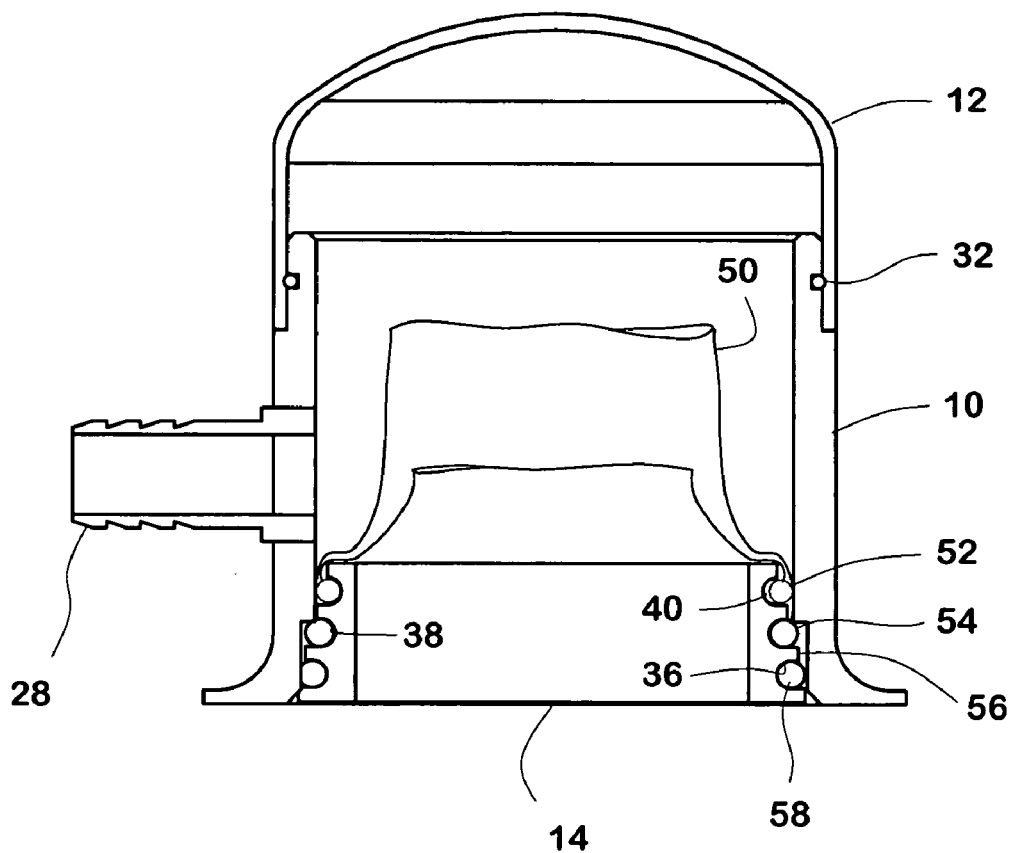
FIG. 2 is a sectional view of the device, assembled, taken on a bisecting longitudinal plane.

As shown in FIG. 1, an external urinary catheter embodying the invention includes a housing 10, a removable cap 12, and a base 14. These parts are preferably machined from ultra-high molecular weight polyethylene (UHMW); however, other materials, and other methods of manufacture, such as injection molding, may prove satisfactory.

The housing 10 has a substantially uniform inner diameter sized to fit over the penis. Its outer surface has a reduced-diameter upper rim 22, a main portion 24, and a lower circumferential flange or brim 26. A hollow tubing fitting 28 is installed in a hole extending through the wall of the main portion. The fitting directs liquid which collects within the device to tubing (not shown) which leads to a bag or other receptacle at a lower elevation. The bag may be worn by the patient, for example, on the leg. For stationary patients, the bag may be attached to a suitable fixture.

A groove for an upper O-ring 32 is formed in the surface of the upper rim.

The cap 12 is a simple piece of uniform thickness, having a cylindrical skirt 34 whose inner diameter is a slip fit over the upper rim of the housing. The upper O-ring 32 presses outwardly against the skirt when the cap is installed, retaining the cap in place and providing a fluid seal.

The base 14 is a ring-shaped element having three external grooves 36, 38, 40. The upper groove 40 is designed to receive the base of a first elastic, flaccid sleeve 50 having a relaxed diameter less than that of the penis, and substantially less than the inside diameter of the base. Removing the distal end from a condom produces a particularly suitable sleeve. The rolled proximal end 52 of the condom is stretched over the shoulder. An additional retainer (not shown) may be provided if desired. A second elastic, flexible sleeve 54 is seated in the middle groove 38. This sleeve is shorter than the first, and is designed to seal around the base of the penis, whereas the first sleeve is designed to seal near the head of the penis. The dual-sleeve arrangement provides particularly reliable leak protection.

O-ring 58 is seated in the bottom groove 36. It is sized to provide a slight interference fit against the counterbore 56 at the bottom of the housing, to keep the parts assembled i.e. defines a means for retaining the base within the lower end of the main portion of the housing.

When the base (with the flaccid sleeve installed) is inserted from below into the housing, the lower O-ring provides a fluid seal against the housing, and also frictionally engages the inner diameter of the housing to hold the parts together. With the cap also in place, the assembly is placed over the penis, over which the sleeve stretches, forming a liquid-tight seal against it. The O-rings prevent leakage between the elements 10, 12 and 14, so that the fitting 28 is the only avenue of escape for urine which enters the housing through the urethra.

The device may be held in place simply by briefs worn over it. Additional retainers may be added as necessary. If desired, an absorbent pad or piece of material may be placed beneath the rim of the device, against the skin, to intercept any leakage when the device is removed, and to prevent chafing against the scrotum.

FIGS. 3–6 show two alternative forms of the invention, which in principle are the same.

Figure 3:
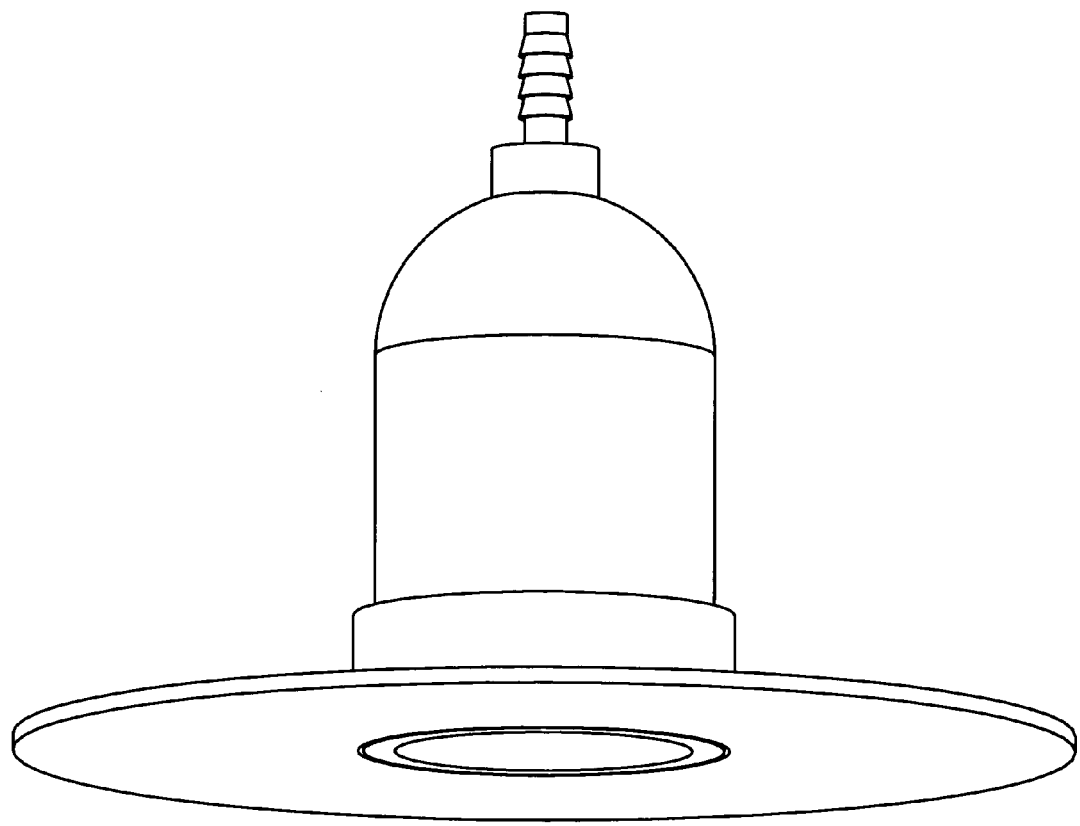
FIG. 3 is a view like FIG. 1 of a second embodiment of the invention.
Figure 4:
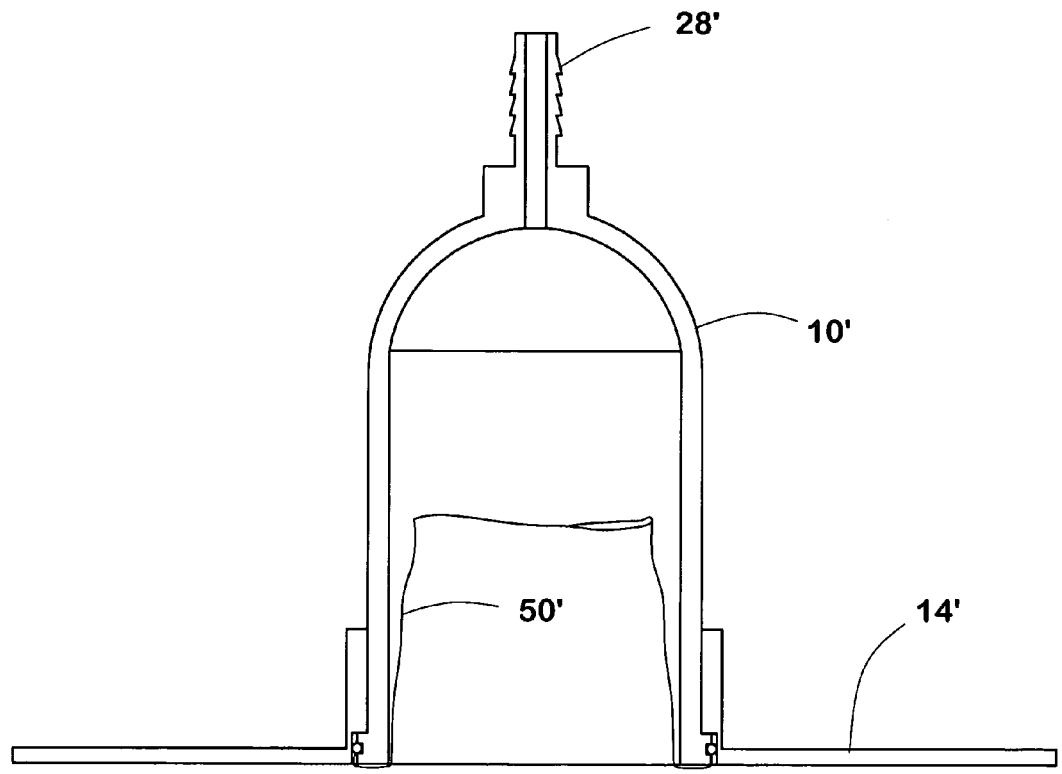
FIG. 4 is a sectional view of the device, assembled, taken on a bisecting longitudinal plane.

The device shown FIGS. 3 and 4 has a longer housing 10', terminating at a fitting 28' which extends along the longitudinal axis of the device. The rolled end of an elastic sleeve 50' may be installed in the external groove at the bottom end of the housing 10'. Preferably, the sleeve is passed down under the bottom end of the housing, then up into it. The base 14' is then pressed onto the housing from above, securing the rolled end of the sleeve in the groove. Friction maintains the assembly.

Figure 5:
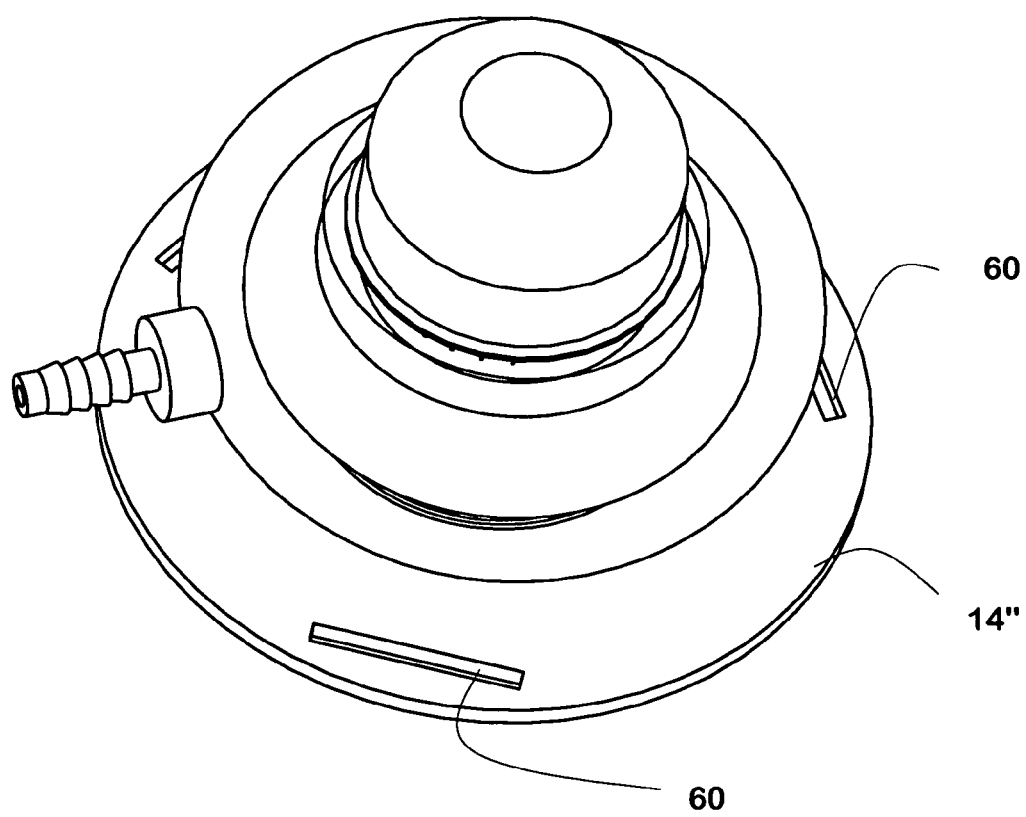
FIG. 5 is a view like FIG. 1 of a third embodiment of the invention.
Figure 6:
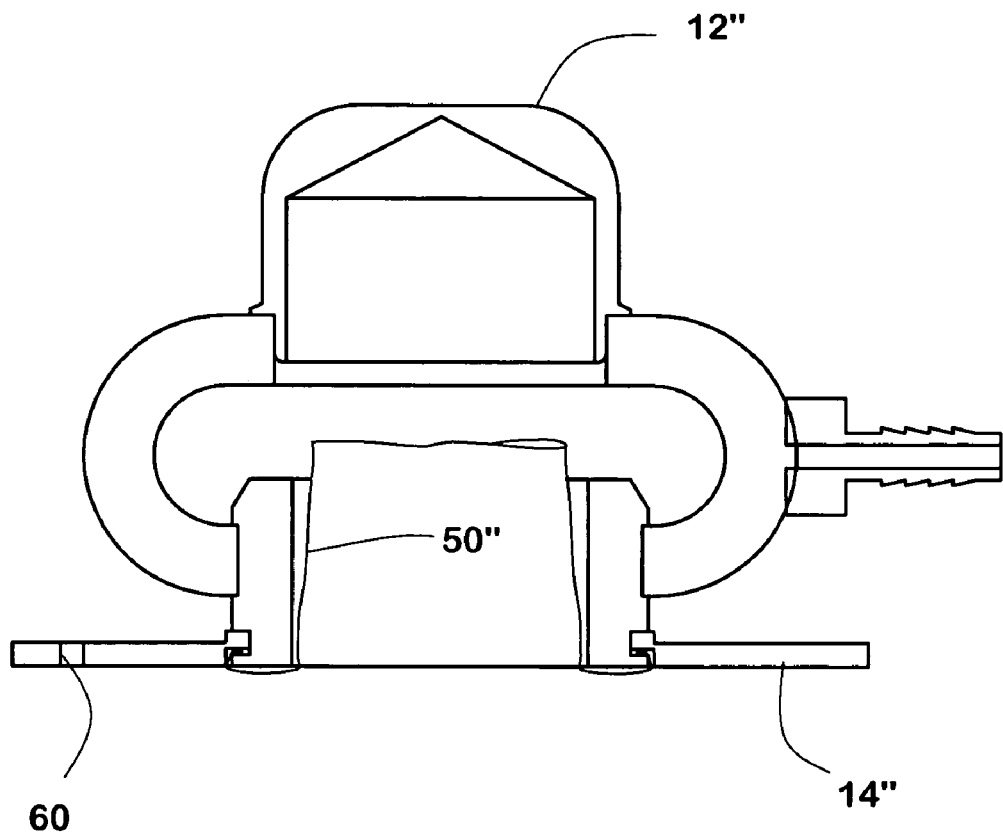
FIG. 6 is a sectional view of the device, assembled, taken on a bisecting longitudinal plane.

In the alternative form of the invention shown in FIGS. 5 and 6, an elastic sleeve 50" again is passed under the bottom of the base 14", which snaps into the housing 10", gripping the rolled bottom of the sleeve. A cap 12" is inserted into a hole at the top of the housing. The slots 60 shown in FIG. 5 are intended to receive elastic retaining straps which may be used to secure the device to the person. Such retainers may, of course, be used with the other embodiments.

I claim:

1. An external urinary catheter comprising
   a housing sized to fit over a penis, said housing having a main portion, and a circumferential flange at a lower end of the main portion,
   a tubing fitting extending through a wall of the main portion,
   a removable base having an inside diameter greater than a diameter of the penis and comprising a ring-shaped element having a first external circumferential groove,
   a first, elastic, flaccid sleeve having a relaxed diameter less than that of the penis and substantially less than said inside diameter and seated in said first groove, and;

means for retaining the base within the lower end of the main portion of the housing, wherein the base further has a second external circumferential groove, and the catheter further comprises a second elastic, flexible sleeve seated in said second groove, said second sleeve being shorter than the first sleeve, for sealing around the base of the penis, to provide redundant sealing.

2. The invention of claim 1, wherein the base has a third external circumferential groove, and the catheter further comprises an O-ring seated in said groove and sized to provide a slight interference fit against the housing, thereby acting as said means for retaining the base.

3. The invention of claim 1, wherein the housing has an open upper end, and the catheter further comprises a cap for closing the upper end of the housing.

\* \* \* \* \*